United States Patent [19]

Casara

[11] Patent Number: 5,380,936
[45] Date of Patent: Jan. 10, 1995

[54] PROCESS FOR PREPARING 4-AMINO-5-HEXENOIC ACID

[75] Inventor: Patrick Casara, Ittenheim, France

[73] Assignee: Merrell Dow Pharmaceuticals Inc., Cincinnati, Ohio

[21] Appl. No.: 184,762

[22] Filed: Jan. 19, 1994

Related U.S. Application Data

[63] Continuation of Ser. No. 986,636, Dec. 7, 1992, abandoned.

[30] Foreign Application Priority Data

Dec. 10, 1991 [EP] European Pat. Off. ........ 91403351.9

[51] Int. Cl.$^6$ ............................................. C07C 229/00
[52] U.S. Cl. ........................................ 562/574; 558/6; 560/172; 560/183; 560/262
[58] Field of Search ........................................ 562/574

[56] References Cited

U.S. PATENT DOCUMENTS

| Re. 31,980 | 9/1985 | Metcalf et al. . |
|---|---|---|
| 3,960,927 | 1/1976 | Metcalf et al. . |
| 4,039,549 | 8/1977 | Metcalf et al. . |
| 4,178,463 | 12/1979 | Gittos et al. . |
| 4,668,433 | 5/1987 | Ochsner . |
| 4,898,977 | 2/1990 | Herold et al. . |
| 4,912,232 | 3/1990 | Mullins et al. . |
| 5,010,189 | 4/1991 | Herold et al. . |
| 5,101,043 | 3/1992 | Steffen . |

FOREIGN PATENT DOCUMENTS

| 0354201 | 2/1990 | European Pat. Off. . |
|---|---|---|
| 0427197 | 5/1991 | European Pat. Off. . |
| 2133002 | 7/1984 | United Kingdom . |

OTHER PUBLICATIONS

Abstract–AAD89–05373, vol. 49/12–B of Dissertation Abstracts International, p. 5280; Tae Woo Kwon: "Part I. Asymmetric synthesis of 4-vinyl-4-aminobutyric acid. Part II. Section A–Thiophenyl cyclopropylcarbinyl derivatives; conversion to dithiophenylcyclobutanes. Section B–Homoallylic substitution reactions'–'–1988–Assignee: The University of Connecticut.

Chemical and Pharmaceutical Bulletin, vol. 26, No. 3, pp. 774–783, Pharmaceutical Society of Japan; M. Watanabe et al.: "Ubiquinone and related compounds. XXXI. Synthesis of urinary metabolites of ubiquinone, phylloquinone, alpha-tocopherol and their related compounds". Mar. 1978, Assignee: Takeda Chemical Industries.

JACS, vol. 98, No. 10, pp. 2901–2910; L. E. Overman: "A general method for the synthesis of amines by the rearrangement of allylic trichloroacetimidates. 1,5 transposition of alcohol and amine functions". May 1976–Assignee: University of Calif.

JACS, Vol. 92, No. 3, pp. 741–743; W. S. Johnson et al.: "A simple stereo-selective version of the claisen rearrangement leading to transtrisubstituted olefinic bonds. Synthesis of squalene". Feb. 1970–Assignee: Stanford University.

Tetrahedron, vol. 44 No. 13, pp. 4243–4258 (1988)–G. Deleris et al.–"Direct regiospecific allylic amination via silicon induced pericyclic reactions. A novel synthesis of gamma vinyl gaba".

Chem. Pharm. Bull. vol. 26, No. 3, pp. 774–783 (1978)–Masazumi Watanabe et al. "Synthesis of urinary metabolites of Ubiquinone, phylloquinone, α-tocopherol and their related compounds".

J. Am. Chem. Soc. vol. 44, pp. 667–668 (1972) E. J. Corey et al. "A new method for the synthesis of macrolides".

*Primary Examiner*—Michael L. Shippen
*Attorney, Agent, or Firm*—Carolyn D. Moon

[57] ABSTRACT

This invention relates to a novel synthesis of 4-amino-5-hexenoic acid by thermal rearrangements, and to the novel intermediates produced thereby.

1 Claim, No Drawings

PROCESS FOR PREPARING 4-AMINO-5-HEXENOIC ACID

This is a continuation of application Ser. No. 07/986,636, filed Dec. 7, 1992, now abandoned.

This invention relates to a novel synthesis of 4-amino-5-hexenoic acid using thermal rearrangement reactions, and to the novel intermediates produced thereby.

4-Amino-5-hexenoic acid, otherwise known as vigabatrin or vinyl GABA is a GABA-T inhibitor marketed under the tradename SABRIL ® for the treatment of epilepsy. (See *review article on vigabatrin* by S. M. Grant, et al in *Drugs*, 41 (6):889–926, 1991 ).

In essence, this process is based upon known thermal reactions starting from erythritol; said thermal reactions being (1) an elimination process for the formation of a double bond, (2) a Claisen rearrangement and (3) an Overman rearrangement. The involved reaction sequence is depicted by the following reaction scheme.

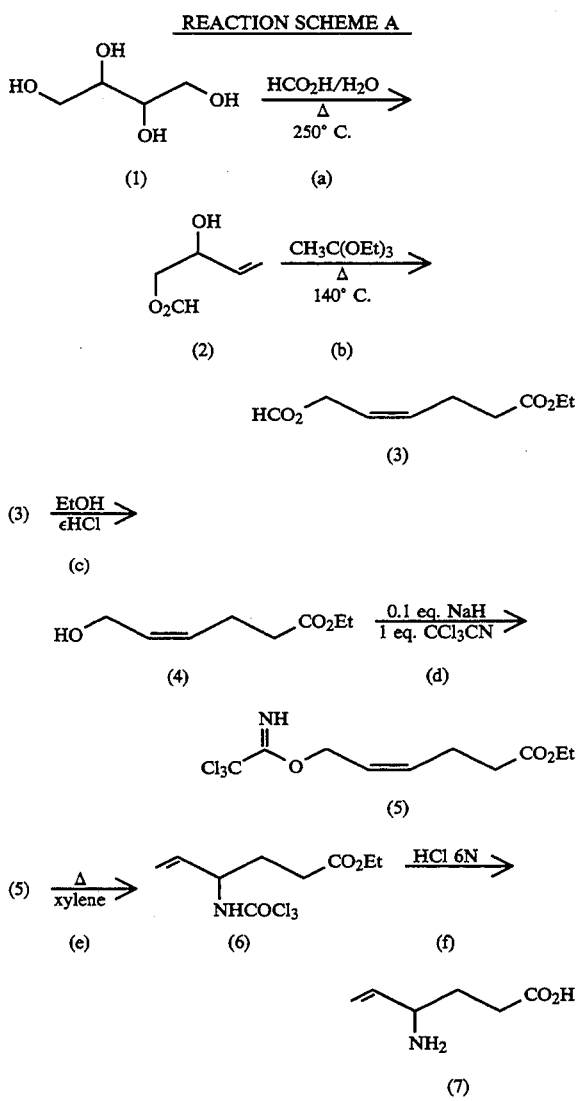

wherein Et is ethyl.

Step (a) of the process involves the known thermal rearrangement reaction for the preparation of 4-formyloxy-3-hydroxy-1-butene (2) from erythritol (1) (see Prevost, C., *Ann. Chem.*[10], 10, 398, 1928). Although no work-up is necessary, better yields of a purer compound may be obtained if the product is re-distilled. Step (b) involves a second thermal rearrangement reaction-followed by a hydrolysis-wherein 4-formyl-3-hydroxy-1-butene is heated at 140°–150 ° C. in the presence of excess quantities of the orthoacetate (4 to 1) under conditions for removal of the in situ produced alcohol. (See Johnson W. and Coll, *J. Am. Chem. Soc.* 92, 741, 1970). Following hydrolysis and removal of the excess orthoacetate, the so-produced product ethyl 6-formyloxy-4-hexanoate may be used as is, or it may optionally be subjected to a distillation for purification or it may be subjected to flash chromatography on $SiO_2$. Alternatively this thermal rearrangement may be effected using one equivalent of the orthoacetate in an inert solvent which boils around 140° to 150° C. (e.g. xylene). The reaction time for these reactions may be monitored by the measurement of the alcohol (methanol or ethanol) which is distilled off.

Step (c) involves the conversion of the formate to its corresponding alcohol by allowing the formate to be stirred at temperatures of about 15° to 25° C. whilst in absolute ethanol to which catalytic quantities of alcoholic HCl gas has been added. Step (d) involves the reaction of trichloroacetonitrile with ethyl 6-hydroxy-4-hexanoate in the presence of catalytic quantities of NaH ($\approx$0.1 equivalent) in an aprotic anhydrous solvent (preferably anhydrous ether) under an inert-gas, preferably nitrogen, at about 0° C. to form an in situ imidate intermediate (5) which, by thermal rearrangement, is converted to ethyl 4-trichloro-acetoamido-5-hexanoate (6); the rearrangement being effected using the techniques of Overman, L. J., *Am. Chem. Soc.* 98, 2901, 1976. The final step involves the hydrolysis of the imidate, preferably by acid hydrolysis but alternatively using basic hydrolysis conditions, to produce the desired 4-amino-hexenoic acid, as its HCl salt. The free acid or other pharmaceutically acceptable salts thereof may be obtained by standard procedures well known in the art.

The advantages of this process may be summarized as follows:

(1) the process does not utilize or form carcinogenic materials, nor are any dangerous reactants or solvents utilized,
(2) the starting material may be prepared from an inexpensive raw material (potato starch),
(3) reaction sequence may be done with only one purification before the final hydrolysis,
(4) a limited number of organic solvents are needed,
(5) the excess of reactants (e.g. trichloroortho-acetate) and solvents (e.g. xylene) may be recovered and re-cyclized,
(6) lack of undesirable by-products,
(7) reactions are facile without problems associated with temperature control and the products may be purified without the need for chromatographic work-up.

The following example illustrates the novel process of this invention.

EXAMPLE 1

4-Amino-5-hexenoic acid

STEP A:
4-FORMYLOXY-3-HYDROXY-1-BUTENE:

A solution of erythritol (50 g, 0.5 mole) in aqueous formic acid (150 g, 75%) was heated above 100° C., 12

H, then water and formic acid were distilled off and the reaction mixture was heated above 200° C. with a Bunsen burner. The product was collected by distillation (b.p. 230° C., 30 g) and should be rectified (b.p. 90° C., 15 mn).

$^1$H NMR (90 MHz) (CDCl$_3$, TMS) δ ppm. 3.23 (s, 1 H, OH), 3.6 (m, 1 H, CH), 4.23 (t, 2 H, CH$_2$), 5.33 (m, 2 H, CH$_2$=), 5.83 (m, 1 H, —CH=), 8.16 (s, 1 H, HCO$_2$).

STEP B: ETHYL 6-FORMYLOXY-4-HEXANOATE:

A solution of 4-formyloxy-3-hydroxy-1-butene (1.06 g, 10 mmol) and propionic acid (1 drop) in triethylorthoacetate (6 g, 40 mmol) was heated at 140° C. under conditions for distillative removal of ethanol. After 2 H, the excess of ethylorthoacetate was removed by distillation in vacuo. The residue was hydrolysed with water and extracted with AcOEt. The product was purified by flash chromatography on SiO$_2$ (eluant AcOEt: hexane, 2:8) (1 g, 60%) but distillative purification is preferred when larger quantities are involved.

$^1$H NMR (90 MHz) (CDCl$_3$, TMS) δ ppm. 1.26 (t, 3 H, CH$_3$, J =6 Hz), 2.4 (s, 4 H, (CH$_2$)$_2$), 4.1 (q, 2 H, CH$_2$, J =6 Hz), 4.6 (d, 2 H, CH$_2$—C=, J =6 Hz), 5.73 (m, 2 H, CH=CH), 8.06 (s, 1 H, HCO$_2$).

STEP C: ETHYL 6-HYDROXY-4-HEXANOATE:

A solution of 6-formyloxy-6-hexanoate (0.9 g, 5 mmol) in absolute EtOH (10 mL) containing few drops of a saturated solution of alcoholic HCL gas was left 2 H at 20° C. The solvent was removed in vacuo and the residue was used for the next step without further purification (0.7 g, quantitative). This compound was found to be partially decomposed by flash chromatography on SiO$_2$.

$^1$H NMR (90 MHz) (CDCl$_3$, TMS) δ ppm. 1.26 (t, 3 H, CH$_3$, J =6 Hz), 2.4 (s, 4 H, (CH$_2$)$_2$), 2.83 (s, 1 H, OH), 4.1 (s, 2 H, CH$_2$—C=) 4.16 (q, 2 H, CH$_3$CH$_2$, J 6 Hz), 5.7 (s, 2 H, CH=CH).

STEP D: ETHYL 4-TRICHLOROACETAMIDO-5-HEXANOATE:

Sodium hydride (0.03 g of a 50% dispersion in oil, 0.5 mmol, was added to a solution of ethyl 6-hydroxy-4-hexanoate (0.7 g, 5 mmol) and trichloroacetonitrile (0.6 g, 5 mmol) in anhydrous ether (50 mL) under N$_2$ at 0° C. After 1 H, ethanol (0.5 mmol) was added and the solvent was removed in vacuo. The formation of the imidate was controlled by NMR (NH, ~8.5 ppm). A solution of the crude imidate in xylene (30 mL) was heated at reflux 48 H. Then the solvent was removed in vacuo and the residue was purified by flash chromatography on SiO$_2$. (eluant AcOEt: hexane, 2:8) to give the title product (1.1 g, ~70%). $^1$H NMR (90 MHz) (CDCl$_3$, TMS) δ ppm. 1.23 (t, 3 H, CH$_3$, J =6 Hz), 2.0 (t, 2 H, CH$_2$—CH$_2$-CO$_2$, J =5 Hz), 2.36 (s, 2 H, CH$_2$CO$_2$), 4.1 (q, 2 H, CH$_3$CH$_2$, J =6 Hz), 4.4 (t, 1 H, CH—CH$_2$, J =5 Hz), 5.1 (m, 2 H, CH$_2$), 5.76 (m, 1 H, CH=CH$_2$), 7.2 (s, 1 H, NH). A sample was distilled for analysis (b.p. 150° C., 0.5 mmHg).

Analysis calculated for C$_{10}$H$_{14}$NO$_3$Cl$_3$: C: 39.69 H: 4.66 N: 4.64 Found: C: 39.87 H: 4.62 N: 4.49

STEP E: 4-AMINO-5-HEXENOIC ACID:

A suspension of ethyl 4-trichloroacetoamido-5-hexanoate (0.3 g, 1 mmol) in 6N HCl (10 mL) was heated under reflux 6 H. Then the mixture was concentrated in uacuo, diluted with water (10 mL), washed twice with Acoet, and dried in uacuo to give the title product (0.18 g, 100%). NMR, TLC (NH$_4$OH:EtOH, 3:7) are identical with those of an authentic sample of 4-amino-5hexenoic acid.

$^1$H NMR (90 MHz) (D$_2$O), δ ppm. (TMS) 1.83 (m, 2 H, CH$_2$CO$_2$), 2.33 (m, 2 H, CH$_2$CH$_2$) 3.66 (m, 1 H, CH—C=), 5.35 (m, 3 H, CH$_2$=CH).

What is claimed is:

1. The process for preparing 4-amino-5-hexenoic acid, or its pharmaceutically acceptable salts thereof which comprises the steps:
    (a) thermally rearranging erythritol to 4-formyloxy-3-hydroxy-1-butene, in the presence of an excess of formic acid,
    (b) thermally rearranging 4-formyloxy-3-hydroxy-1-butene to ethyl 6-formyloxy-4-hexanoate, followed by the conversion of the formate to its corresponding alcohol ethyl 6-hydroxy-4-hexanoate,
    (c) converting the so-produced ethyl 6-hydroxy-4-hexanoate to ethyl 6-trichloroacetimidoxy-4-hexanoate by reaction with trichloroacetonitrile, followed by its thermal rearrangement to ethyl-4-trichloroacetamido-5-hexanoate which, by hydrolysis is converted to the desired 4-amino-5-hexenoic acid, and optionally converting said acid to a pharmaceutically acceptable salt thereof.

* * * * *

UNITED STATES PATENT AND TRADEMARK OFFICE
CERTIFICATE OF CORRECTION

PATENT NO. : 5,380,936
DATED : January 10, 1995
INVENTOR(S) : Patrick Casara

It is certified that error appears in the above-indentified patent and that said Letters Patent is hereby corrected as shown below:

At Column 2, line 11, the patent reads "4-hexanoate" and should read --4-hexenoate--.

At Column 3, lines 10 and 26, the patent reads "4-HEXANOATE" and should read --4-HEXENOATE--, and in line 27, the patent reads "6-hexanoate" and should read --6-hexenoate.

At Column 3, lines 38-39, the patent reads "J 6 Hz" and should read --J=6 Hz--.

At Column 3, line 41, the patent reads "5-HEXANOATE" and should read --5-HEXENOATE--, and in lines 44-45, the patents reads "4-hexanoate" and should read --4-hexenoate--.

At Column 4, lines 17-18 and 44, the patent reads "5-hexanoate" and should read --5-hexenoate.

At Column 4, lines 20 and 21, the patent reads "uacuo" and should read

At Column 4, Claim 1, lines 37, 39, 40-41, and 41-42, the patent reads "4-hexanoate" and should read --4-hexenoate--.

Signed and Sealed this

Twenty-third Day of July, 1996

*Attest:*

BRUCE LEHMAN

*Attesting Officer*          Commissioner of Patents and Trademarks